United States Patent [19]
Rump et al.

[11] Patent Number: 5,217,692
[45] Date of Patent: Jun. 8, 1993

[54] GAS SENSOR ARRANGEMENT

[75] Inventors: Hanns Rump, Unna-Massen; Claus-Dieter Kohl, Herzogenrath, both of Fed. Rep. of Germany

[73] Assignee: E.T.R. Elektronik Technologie Rump GMBH, Dortmund, Fed. Rep. of Germany

[21] Appl. No.: 689,857

[22] Filed: Jun. 10, 1991

[30] Foreign Application Priority Data

| Oct. 17, 1989 | [DE] | Fed. Rep. of Germany | 3934532 |
| Jun. 23, 1990 | [DE] | Fed. Rep. of Germany | 4020113 |
| Aug. 8, 1990 | [JP] | Japan | 4025117 |
| Aug. 31, 1990 | [JP] | Japan | 4027547 |

[51] Int. Cl.$^5$ ............................................. G01N 27/00
[52] U.S. Cl. ............................................. 422/98; 422/94; 73/25.23; 73/31.05; 73/31.06
[58] Field of Search ............. 422/94, 98; 73/23.2, 73/25.03, 31.05, 31.06; 338/34; 340/632

[56] References Cited

U.S. PATENT DOCUMENTS

| 3,200,011 | 8/1965 | Baker | 422/94 |
| 3,748,625 | 7/1973 | Bennewitz | 338/35 |
| 3,865,550 | 2/1975 | Bott et al. | 422/98 |
| 4,224,289 | 9/1980 | Takahama et al. | 422/98 |
| 4,338,281 | 7/1982 | Treitinger et al. | 422/98 |
| 4,381,922 | 5/1983 | Frey et al. | 422/98 |
| 4,396,899 | 8/1983 | Ohno | 73/31.06 |
| 4,574,264 | 3/1986 | Takahashi et al. | 338/34 |
| 4,587,104 | 5/1986 | Yannopoulos | 422/94 |
| 4,654,624 | 3/1987 | Hagan et al. | 338/34 |
| 4,731,226 | 3/1988 | Takahata et al. | 422/98 |
| 4,849,180 | 7/1989 | Fukui | 422/98 |
| 4,928,513 | 5/1990 | Sugihara et al. | 73/31.06 |
| 4,938,928 | 7/1990 | Koda et al. | 422/98 |
| 4,972,433 | 12/1990 | Katsura et al. | 422/98 |
| 5,082,789 | 1/1992 | Morrison et al. | 436/132 |

FOREIGN PATENT DOCUMENTS

| 2816331 | 11/1978 | Fed. Rep. of Germany | 422/94 |
| 0073661 | 5/1982 | Japan | 422/94 |
| 0050353 | 3/1984 | Japan | 422/94 |
| 2014047 | 1/1987 | Japan | 422/98 |

Primary Examiner—Robert J. Warden
Assistant Examiner—T. A. Trembley
Attorney, Agent, or Firm—Herbert Dubno

[57] ABSTRACT

A gas sensor arrangement has at least a first sensor element which is primarily sensitive towards oxidizable gases and generates a corresponding measuring signal and an electric control and evaluation unit, wherein the measuring signal generated by the first sensor element is evaluated. In order to avoid inaccuracies when in addition to the oxidizable gases at the same time also reducible gases are present, the gas sensor arrangement is provided with at least one second sensor element, which is primarily sensitive to reducible gases and generates a corresponding measuring signal, which is fed to the control and evaluation unit for evaluation.

23 Claims, 4 Drawing Sheets

GAS SENSOR ARRANGEMENT

CROSS REFERENCE TO RELATED APPLICATION

This application is a national phase of PCT/EP 90/10752 filed Oct. 17, 1990 and based, in turn, on German national applications P39 34 532.7 of Oct. 17, 1989, P 40 20 113.9 of Jun. 23, 1990, P 40 25 117.9 of Aug. 8, 1990 and P 40 27 547.7 of Aug. 31, 1990, under the International Convention.

FIELD OF THE INVENTION

The invention relates to a gas sensor arrangement with at least a first sensor element which primarily is sensitive towards oxidizable gases and generates a corresponding measuring signal and an electric control and evaluation unit in which the measuring signal of the first sensor element is evaluated.

BACKGROUND OF THE INVENTION

The necessity to detect gases in the air has become increasingly important of late.

For instance, it is desirable to trigger switching processes depending on the presence of noxious substances in the air. Particularly in connection with motor-vehicle ventilation, numerous efforts have been made to act upon the ventilation system of a vehicle by means of a sensor sensitive to gas, so that when an unusually high load of noxious substances is present in the surrounding air, the fresh air supply to the vehicle is interrupted and the system is switched, for instance, to air recirculation.

It is known to detect certain gases with the aid of metal oxide gas sensor elements. The sensor element here consists mostly of a metal oxide, which is brought to a working temperature by suitable heating.

Tin dioxide sensor elements heated to a temperature of approximately 250° C. to 450° C. are widely used. As a rule, a substance acting as a catalyst is admixed with the tin dioxide, for instance, platinum, palladium and rhodium.

Sensor elements of this kind experience a resistance reduction in the presence of oxidizable gases and the tin dioxide releases oxygen. When the sensor is again exposed to normal air, the surface reacts again with the oxygen to form tin dioxide. Thus, the process is reversible and the sensor is not subject to wear.

It has been found that sometimes a rough difference occurs between the expected resistance value of the sensor and the concentration of oxidizable gas, e.g. carbon monoxide. More detailed research has shown now that in the simultaneous presence of reducible gases, these gases have a strong influence on the reaction between the reducible gases and the sensor surface.

In extreme cases in spite of high concentration levels, no reaction or only a minimal electric reaction will take place in the sensor. As an example, reference can be made to the reaction in the simultaneous presence of carbon monoxide (CO) and nitrogen oxide (NOx). The cause is the direct mutual reaction of the gases close to the hot sensor surface, whereby the catalytic substance is influenced.

A particular disadvantage of the aforementioned heated tin dioxide sensor is its low sensitivity with respect to diesel exhaust gases. This appears to be due to the fact that tin dioxide sensors always react with a resistance reduction in the presence of an oxidizable gaseous substance. So for instance, tin dioxide sensors react to carbon monoxide, peroxide or gasoline vapors correspondingly to bar 60 in FIG. 1. These components are present in the exhaust gases of engines running on gasoline, so that this clear reaction of the tin dioxide sensor occurs.

Figure 1:
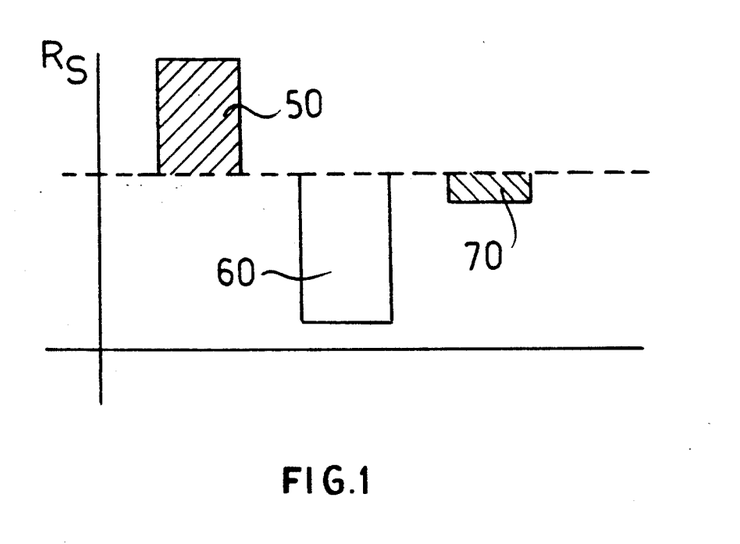
FIG. 1 is a bar graph illustrating a problem attacked by the invention.

If this tin dioxide sensor is exposed to nitrogen oxides (NOx) in the laboratory, its inner resistance increases, as shown by bar 50 in FIG. 1.

In the exhaust gases of a Diesel engine particularly when it runs under load, the substances corresponding to bar 60 in FIG. 1 coexist with the ones corresponding to bar 50 in FIG. 1. As a result, it has been found that the tin dioxide sensor reacts less clearly than one would expect based on the measured and proven proportions of the gases which are resent. The reaction of the tin dioxide sensor corresponds to bar 70 in FIG. 1.

This is highly disturbing for the sensor operation, since when such sensors are used in practice, they are very often exposed simultaneously to oxidizable as well as reducible gases.

OBJECT OF THE INVENTION

It is the object of the present invention to provide a reliable detection of the target substance, even when the aforementioned mixtures are present.

SUMMARY OF THE INVENTION

According to the invention, this object is achieved by providing the sensor with at least one second sensor element which is primarily sensitive towards reducible gases and generates a corresponding measuring signal, which is fed to the electric control and evaluation unit.

According to the invention, the sensor comprises one or more metal-oxide sensor elements and in addition one or more phthalocyanine sensor elements, whereby the signals of all sensor elements are evaluated in the evaluation unit so that the opposite influences of simultaneously present reducible and oxidizable gases are canceled due to the fact that in the evaluation unit the signals of the metal-oxide sensor element, or elements are tied in with the signals of the phthalocyanine sensor element, or elements corresponding to a function stored in the evaluation unit.

The air temperature and/or air humidity can additionally be established through appropriate sensor elements, and are fed additionally to the evaluation unit, whereby the specific influence of these parameters are also present as a correction function in the evaluation unit and the signals of these sensors are built in as correction values according to the function.

At least one metal-oxide sensor element and at least one phthalocyanine sensor element are preferably arranged on a common heated carrier, but are separated thermally from each other by a $SiO_2$ separation gap.

Polysilicon can serve as the carrier material for the sensor elements, whereupon the sensor elements are applied by a thin-film process.

Alternatively aluminum oxide can serve as carrier material for the sensor elements, whereupon the sensor elements and a required heating device are applied by thick-film process.

The metal oxide sensor element can be a tin dioxide sensor element.

For the detection of oxidizable gases in a complex gas mixture, at least one first sensor element is sensitive to oxidizable gases and is preferably a tin dioxide sensor element, the second sensor element serving especially for the detection of nitrogen oxides consists of a heated vanadate or of a heated vanadium pentoxide and the common electronic evaluation unit factors in the electric signals of the sensor elements Fe or Cr or W can be added to the vanadate or the vanadium pentoxide.

The second sensor element can consist of oxides having trivalent metals as constituents or containing admixtures, e.g. of $SNO_2+In_2O_3$, with $In^{3+}$ as admixture.

A second sensor element can consist of a mixture of chromium oxide and niobium oxide.

At least a second sensor element can thus consist of a mixture of chromium oxide in a proportion of 90% and niobium oxide 10%.

The second sensor element can be a gas sensor element of the n-conductive type on the basis of a homogeneous semiconductor and consists of metal oxide in the gas-sensitive layer. The second sensor element can consist of reduced tin oxide in the gas-sensitive layer. The second sensor element can have catalytic admixtures and a thin precious metal coating can be applied to the gas-sensitive layer. Specifically the second sensor element can be enclosed by a heated wire of a catalytic material such as platinum, gold, rhodium or palladium.

The second sensor element can consist of tin dioxide with catalytic admixtures, zinc oxide with catalytic admixtures or iron oxide with catalytic admixtures. In the second sensor element palladium, platinum, rhodium or gold can be used as admixtures.

The second sensor element can be primarily sensitive towards $NO_2$ and is built as a heated molybdate semiconductor, as a heated zirconium semiconductor or as a Clark cell with a solid electrolyte, on whose side, or sides facing the gas access a transition metal can be disposed in fine dispersion and which are provided with electrodes for measuring the conductivity.

The second sensor element here can use platinum or palladium are used as transition metals. The molybdate can contain bismuth additives or iron additives, and the molybdate can be is sintered.

Basically, the invention uses the finding that phthalocyanine is particularly suited for the detection of reducible gases (e.g. NOx). Based on the relative low working temperature of these sensor elements, the cross-sensitivity to oxidizable gases is low.

Therefore, the invention evaluates at the same time signals of a metal oxide sensor element, e.g. on a tin dioxide basis, as well as the signals of a phthalocyanine sensor element.

BRIEF DESCRIPTION OF THE DRAWING

The above and other objects, features and advantages of the present invention will become more readily apparent from the following description, reference being made to the accompanying drawing in which.

SPECIFIC DESCRIPTION

Figure 2:
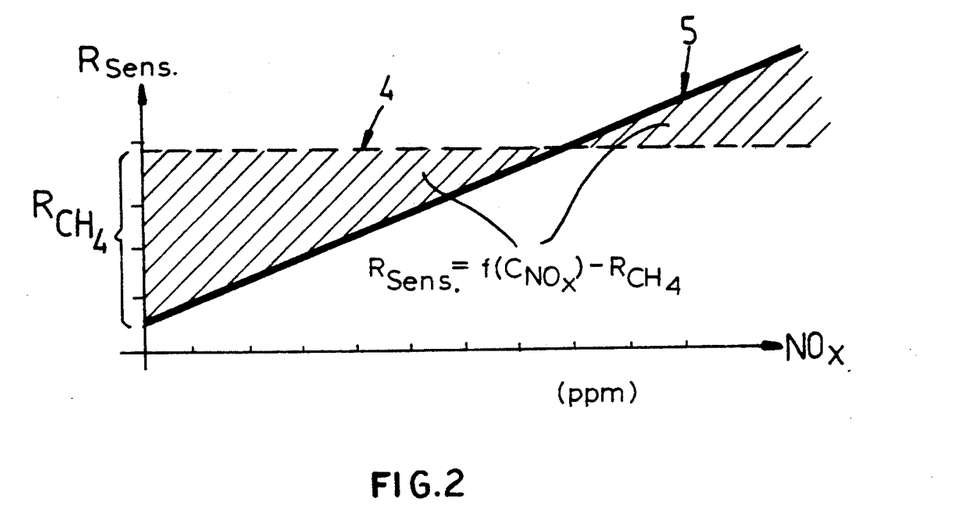
FIG. 2 is a graph of sensor sensitivity.

FIG. 2 shows the basic interrelationship, whereby the inner sensor resistance 5 is shown in the presence of a constant concentration of methane ($CH_4$) and a variable concentration of nitrogen oxide ($NO_2$). The sensor resistance in the presence of normal air is marked 100% resistance value.

Figure 3:
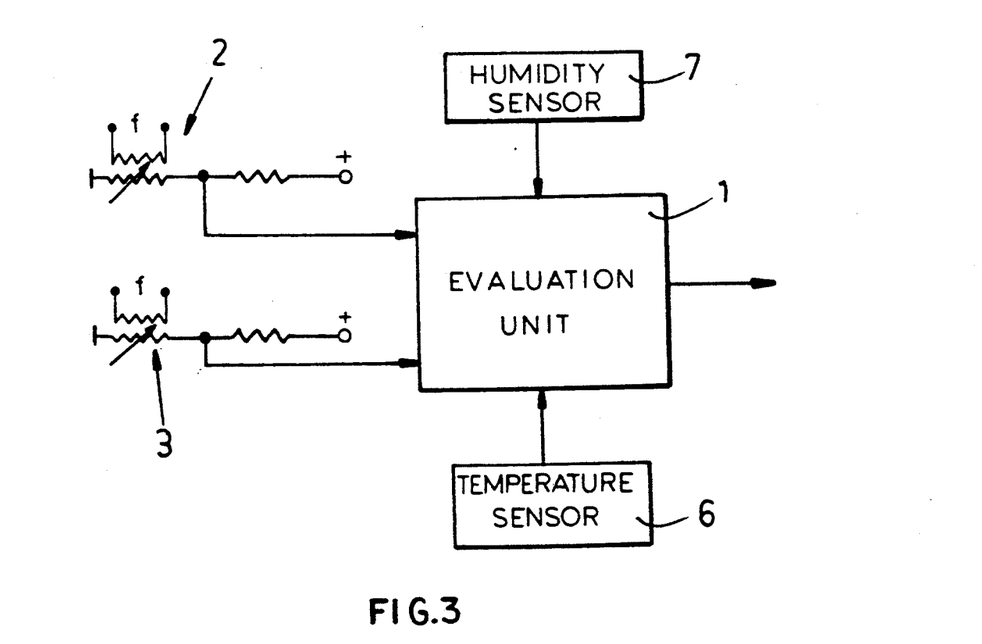
FIG. 3 is a circuit diagram of the system of the invention.

FIG. 3 is a basic representation of an embodiment of the invention. An evaluation unit 1 reads the signals resulting from the connection in series of the sensor elements with an external resistance. The sensor 2 is a tin dioxide sensor which detects oxidizable gases and the sensor 3 is a phthalocyanine sensor, reacting to reducible gases.

In the evaluation unit, which advantageously has the program-controlled use of a microprocessor, the two signals are computed in combination.

Based on FIG. 2—the sensor signal of the tin dioxide sensor 2 is freed by computation (analog or digital) from the influences of the oxidizing gases, which at the same time generate signals at the phthalocyanine sensor 3.

When the signal evaluation includes at the same time also temperature and air-humidity information, the cross-influences of temperature and air humidity can also be compensated. Therefore, in FIG. 3 a humidity sensor 7 and a temperature sensor 6 are shown. Since the respective influence on the corresponding sensor is known, it can for instance be incorporated in a correction table in the evaluation unit 1 and taken into consideration.

Advantageously the tin dioxide sensor 2 and the phthalocyanine sensor 3 can be mounted on a common carrier material, but thermally separated. In the preferred solution, polysilicon is used as the carrier; the polysilicon can be used directly as a heating element by applying an electric voltage. Advantageously, such an arrangement insures reproducible thermal conditions for both types of sensors, thereby increasing the measuring reliability.

It is an advantage of the invention that it prevents the detectable oxidizable gases from being masked by the simultaneous presence of reducible gases, thereby preventing them from remaining undetected or being faultily detected.

Figure 4:
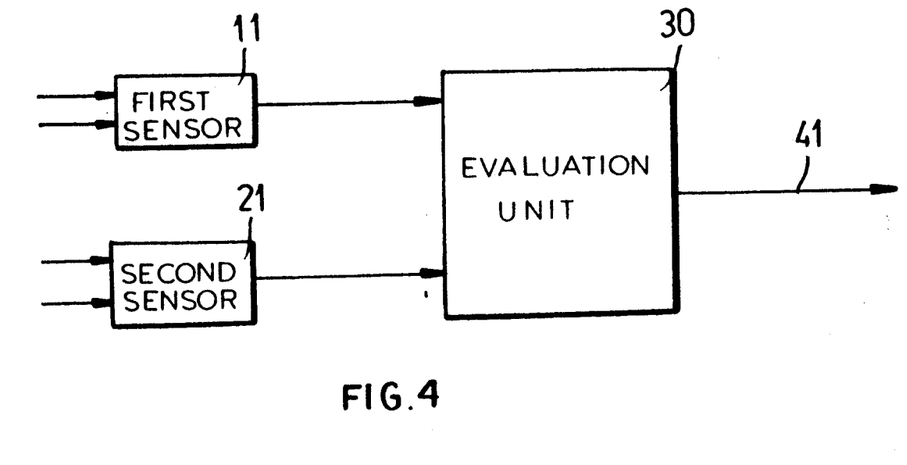
FIG. 4 is a block diagram of the system.
Figure 5:
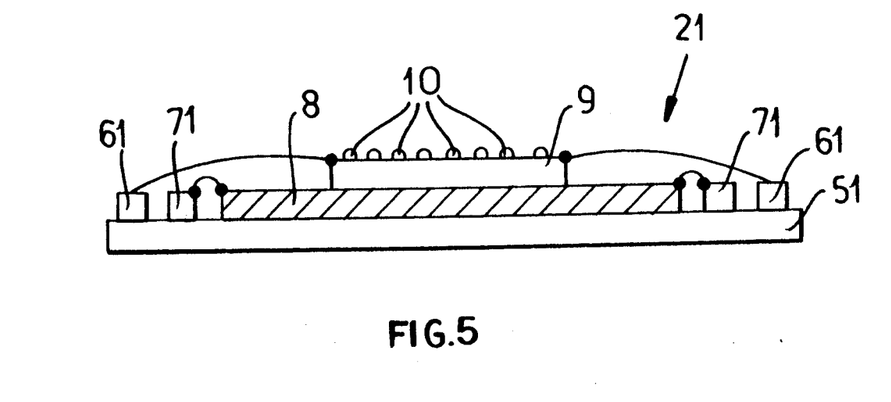
FIG. 5 is a cross sectional view of a sensor.

In the embodiment of the invention shown in FIGS. 4 and 5, a first sensor element 11 for the detection of oxidizable substances, e.g. a tin dioxide sensor element like the one in the aforedescribed embodiment, is combined with a second sensor element 21, whereby the gas-dependent electric output signals are directed to an electric evaluation unit 30, preferably consisting of a microprocessor.

The evaluation of the signal of the first sensor element 11 is factored by considering the signal of the second sensor element 21, e.g. according to the expression $$SA = (S1xx) + (S2xy),$$

whereby SA is the output signal, S1 is the signal of sensor element 11, S2 the signal of sensor element 21, x a factor and y a factor.

The output signal SA is made available at output 41.

The second sensor element 21 consists of an arrangement wherein nitrogen oxides are catalytically cracked ($NO_2 \rightarrow NO+O$), whereby the oxygen is received into the crystal lattice of an appropriate substance which allows for a high mobility of oxygen atoms, thereby modifying the electric resistance value. The second sensor element 21 has a carrier 51 made of $Al_2O_3$ or silicon, bearing a heating layer 8 consisting of platinum heating strips or of polysilicon The heating current is supplied via contacts 71. To the heating layer 8 a layer of the actual sensor part 9 of the second sensor element 21 is applied, which is connected via contacts 61.

A catalyst 10 made of catalytically acting material, e.g. platinum or palladium, is finely distributed on the sensor part 9. The sensor part 9 of sensor element 21 is made of vanadate.

Alternately, vanadium pentoxide can be advantageously used for the sensor part 9, since it is an oxide with high O-mobility.

In order to improve the catalysis (oxygen transport), if necessary Fe, Cr, or W can be added to the vanadate or vanadium pentoxide. Admixing between 0.5%–5% leads to a lasting improvement of reaction properties.

Furthermore, an embodiment is possible wherein the second sensor element 21, or its sensor part 9 consists of oxides containing trivalent metals as constituents or as admixtures, e.g. Chromium oxide and niobium oxide with $Cr^{3+}$ as constituents, or $SNO_2 + In_2O_3$ (ITO) with $In^{3+}$ as admixture, whereby the trivalent metals serve as adsorption position for a preferred adsorption of NO, or $NO_2$.

In a further variant, the second sensor 21, or its sensor part 9 is made of chromium oxide, containing approximately 10% admixture of niobium oxide At working temperatures of approximately 300° C., this material is extremely sensitive to NO, and at the same time insensitive to CO or $CO_2$.

The first sensor element 11 and the second sensor element 21 are preferably mounted on a common carrier. Advantageously, this carrier should also support the evaluation unit 3.

In addition to the materials most often selected for the second sensor 21, besides tin also zinc and iron can be used. Also, the suitability of mixtures of tin dioxide and zinc oxide with various catalytic admixtures have been studied. The basic construction corresponded thereby to the known construction of gas sensors.

The metal oxide was applied on the surface and electrically connected so that the resistance of the metal oxide could be measured. Separated by an electric isolator, underneath this layer is a heating element, which can heat the surface of the metal oxide to values between 150° C. and 400° C.

Figure 6:
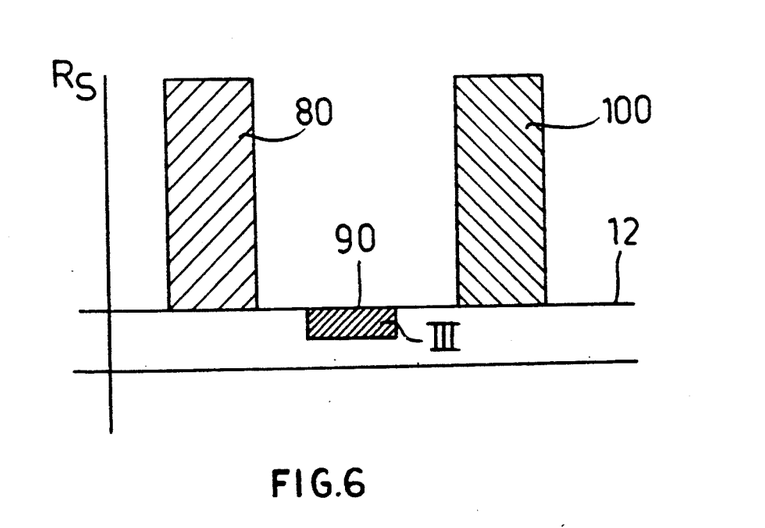
FIG. 6 is another bar graph.

Measurement results which basically are represented in FIG. 6 have been obtained with the following materials.

FIG. 6 shows:
a/ an unusually low sensor resistance 12 with respect to usual tin dioxide sensors in the presence of clean air;
b/ a clear reaction of the sensor element in the presence of nitrogen oxides, as results from bar 60;
c/ a small reaction in the presence of exhaust gases from Otto-carburetor engines, as resulting from bar 90;
d/ a clear reaction of the sensor element to Diesel exhaust gases, as resulting from bar 100.

Figure 7:
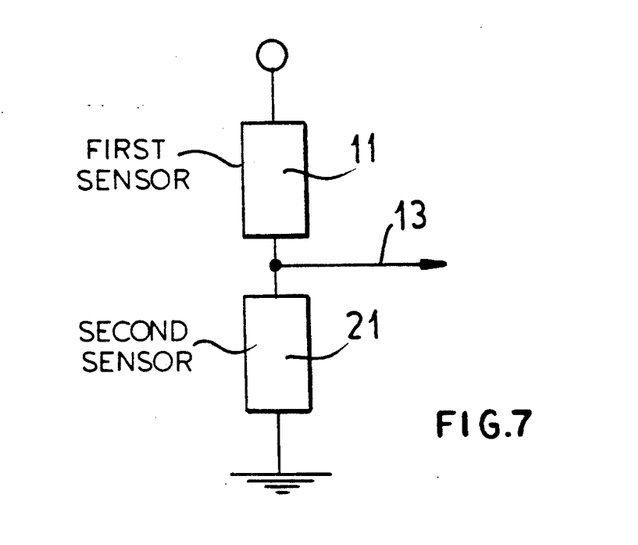
FIG. 7 is a diagram of a sensor connection circuit.

This shows that a gas sensor arrangement having a usual first tin dioxide sensor element 11 combined with the second sensor element 21 designed according to the invention and whose modus operandi is represented in FIG. 6, in a wiring arrangement either similar to FIG. 4 or to FIG. 7, has very good results when used in motor vehicles.

FIG. 7 shows a basic representation which uses the fact that the aforedescribed second sensor element 21 of the invention has a very low inner resistance in the presence of clean air. Hereby, the first tin dioxide sensor element 11 and the second sensor element 21 designed according to the invention form a voltage divider. Its tap makes an electric signal available which independently of the aforedescribed masking effect, delivers a switch signal which furnishes useful results in Diesel as well as in Otto-carburetor engines.

For the second sensor element having the characteristics shown In FIG. 6, the following sensor materials were used:
a/ tin dioxide or reduced tin dioxide with admixtures of catalytic materials. In the tested embodiments, 1 to 15% palladium was added to the tin dioxide.
b/ As in a/, but the palladium was replaced by platinum. In a tested embodiment, tests were carried out with a catalytic admixture between 1-10% platinum.
c/ iron oxide with 1-20% palladium as catalytic admixture.
d/ a mixture of tin dioxide, zinc oxide and palladium. Tested were approximately 50% tin dioxide, 40% zinc oxide and 1-10% palladium.
e/ Further it is proposed to provide a thin layer of precious metal such as gold or platinum on the sensor material by vapor deposition or sputtering. Oxidizable substances react under the influence of catalysts with atmospheric oxygen and do not reach the sensor material.
f/ Wire or wire spirals, preferably of catalysts, optionally heated, are arranged in the proximity of the sensor surface, in order to oxidize oxidizable substances with the atmospheric oxygen. The purpose corresponds to e/.
e/ It is a common feature of all sensor materials that they are semiconductors of the n-conductive type (as opposed to the phthalocyanine sensors which are of the p-conductive type).

A tin dioxide sensor element operating according to the usual standards is combined with gas sensors of the usual construction, whereby the sensor element of the latter gas sensor is n-conductive and consist of tin dioxide with catalytic admixtures, zinc oxide with catalytic admixtures, a mixture of tin dioxide and zinc oxide with catalytic admixtures and an iron oxide with catalytic admixtures.

As catalytic admixture palladium platinum or rhodium are proposed.

The invention can be successfully applied everywhere gases have to be detected and where the danger exists that oxidizable gases coexist with oxygen-carrying gases, e.g. nitrogen. Here, it can be advantageously applied especially in Environmental Engineering.

A further embodiment of the invention uses the fact that, in the presence of a catalyst, (e.g. platinum or palladium) $NO_2$ which is the main culprit for the aforementioned masking effect, is dissociated into NO+O. The dissociation energy is much lower than the dissociation energy required for cracking an $O_2$ molecule. If such a catalyst is applied as cluster or crystallite to the surface of a gas-sensitive substance, any available $NO_2$ will be decomposed in NO+O.

While NO is immediately released back into the atmosphere at temperatures of 250° C., the remaining oxygen atoms generate on the surface a very high virtual oxygen pressure. This means that the density of the oxygen atoms on the surface corresponds to an oxygen pressure higher by several orders of magnitude in the gas space before the test surface (see also B. A. Banse and B. E. Koehl, Surface Science 232 (1990), Pages 275-285).

If the sensor material were tin dioxide, practically no provable effect would result, since only few oxygen vacancies are available and their filling can hardly be proven.

If slightly reduced tin dioxide $SnO_{(2-x)}$ is used, at first a proven effect results, but after a short use the oxygen vacancies are filled and the detection sensitivity disappear.

In the subsequently described embodiment of the invention, the sensor material is supposed to use the above-mentioned effect, whereby many $O_2$-vacancies would be available.

From "Sensors and Actuators", 19 (1989) Pages 351-370, it is known that molybdate is capable of receiving oxygen into crystal lattice and as a result of modifying the electric resistance value.

At a temperature between 300° C. and 400° C. molybdate is capable of recovering oxygen not only into the border layer, but into the entire volume. Explained in a simplified manner, the following reaction takes place:

The available $NO_2$ is decomposed at the catalyst into $NO+O$. The oxygen produces on the surface of the molybdate sensor a high virtual oxygen pressure and is incorporated into the crystal lattice of the molybdate, whereafter the resistance of the molybdate is considerably reduced.

This effect has been noticed when the molybdate contains bismuth or iron additives. It is proposed to preferably sinter the molybdate. The catalytic material facing the side of the gas access can be platinum or palladium.

It has also been established that an oxygen sensor corresponding to the state of the art delivers an output signal when it is triggered by $NO_2$, when on the surface a heated catalytic layer is provided. For this reason it is proposed to use alternately as a sensor element a heated zirconium oxide sensor element, on whose surface also a transition metal (catalyst) has been deposed in a fine dispersion.

An oxygen sensor based on the Clark principle with a solid electrolyte will work following the same procedure, as long as it is brought to the corresponding temperature. For this reason, it is proposed to use a Clark sensor cell with solid electrolyte, when on the surface facing the gas heated transition metals have been deposed in fine dispersion.

Figure 8:
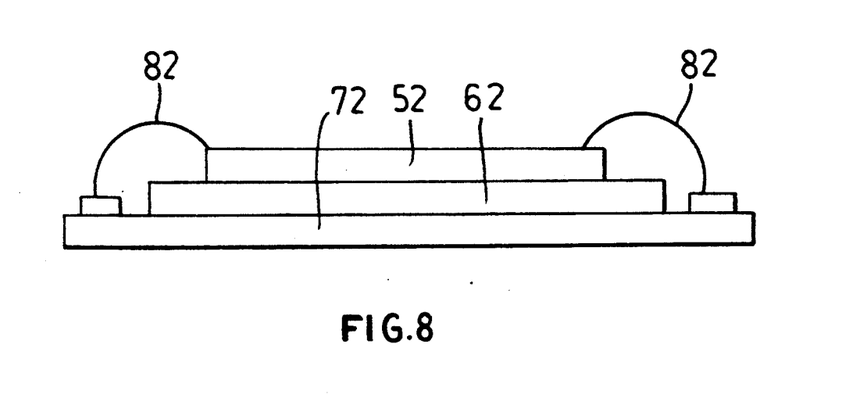
FIG. 8 is a section of another sensor.

The preferred embodiment has a construction as shown in FIG. 8. A carrier 72 is made of aluminum oxide or silicon. A heating device 62 is provided thereon, consisting of coiled platinum applied in by thin- or thick-film technique. Isolated therefrom, the actual sensor material 52, e.g. a bismuth molybdate, is applied. Via contacts 82, the electric resistance value of the molybdate becomes measurable.

The $NO_2$ responsible for the masking effect is cracked into $NO+O$. The oxygen atom is built into the crystal lattice of the sensor material, so that a change in the resistance value occurs. An iron or bismuth molybdate, a zirconium oxide element or a Clark cell are proposed as sensor material. On the gas-facing side of these sensor elements a catalyst of platinum or palladium is applied, which triggers the cracking of the $NO_2$ under temperature influence.

The invention is advantageously used when due to the simultaneous presence of $NO_2$ and oxidizable gases, such as CO or HC, the sensor assigned for measurements delivers false measuring signals due to the aforedescribed masking effect.

The measured value of the $NO_2$ sensor compensates in the electric evaluation and control unit the measured value of the leading sensor falsified by the masking effect, this leading sensor can for instance be a usual tin dioxide gas sensor.

We claim:

1. A gas sensor system for he detection of an oxidizable gas in the presence of a reducing gas capable of masking the detection of said oxidizable gas, comprising:
   first sensor sensitive to an oxidizable gas which generates a signal representative of the concentration of the oxidizable gas, said signal capable of being masked by a reducible gas;
   a second sensor sensitive to said reducible gas; and
   a signal evaluator connected to said first and second sensors and provided with logic circuitry which eliminates from said signal any falsifying effect which may be created by the reducible gas thereby providing an output representing a true concentration of said oxidizable gas.

2. The system defined in claim 1 wherein said second sensor includes at least one phthalocyanine sensor element and said first sensor comprises at least one metal-oxide sensor element, all of said sensor elements having respective outputs connected to said logic circuitry for logically combining outputs of said at least one phthalocyanine sensor element with outputs of said at least one metal-oxide sensor element and thereby providing at an output of said logic circuitry a measure of oxidizable gas concentration.

3. The system defined in claim 2, further comprising an air temperature sensor element and an air humidity sensor element connected to said logic circuitry for correcting the output of said logic circuitry in accordance with air temperature and humidity, respectively.

4. The system defined in claim 2 wherein said at least one metal-oxide sensor element and said at least one phthalocyanine sensor element are provided on a common heatable carrier separated thermally form one another by a $SiO_2$ gap.

5. The system defined in claim 2 wherein at lest one of said sensor elements is a thin-film sensor element applied to a polysilicon carrier.

6. The system defined in claim 2 wherein at lest one of said sensor elements is a thick-film sensor element applied together with a heater to an aluminum-oxide carrier.

7. The system defined in claim 2 wherein at least one of said metal oxide sensor elements is a tin-oxide sensor element.

8. The system defined in claim 1 wherein said first sensor comprises at least one tin-oxide sensor element and said second sensor is at lest one heated vanadate or vanadium-pentoxide sensor element responsive to the presence of nitrogen oxides.

9. The system defined in claim 8 wherein said second sensor contains iron, chromium or tungsten.

10. The system defined in claim 8 wherein said second sensor contains oxides of trivalent metals or mixtures thereof and includes $SnO_2$, $In_2O_3$ and $In^{3+}$.

11. The system defined in claim 10 wherein said second sensor includes at least one second sensor element comprised of a mixture of chromium oxide and niobium oxide.

12. The system defined in claim 10 wherein said mixture consists essentially of 90% chromium oxide and 10% niobium oxide.

13. The system defined in claim 10 wherein said second sensor comprises at least one second sensor element comprised of an n-conductivity homogeneous semiconductor and a metal oxide gas-sensitive layer.

14. The system defined in claim 13 wherein said metal oxide gas-sensitive layer is reduced tin oxide.

15. The system defined in claim 13 wherein said second sensor element contains catalytic additive and a noble metal layer.

16. The system defined in claim 15 wherein said at least one second sensor element is composed of a heated wire of a catalytic material covered by platinum, gold, rhodium or palladium.

17. The system defined in claim 13 wherein said at least one second sensor element is composed of tin dioxide containing catalytic additives, zinc oxide with catalytic additives or iron oxide with catalytic additives.

18. The system defined in claim 13 wherein said at least one second sensor element comprises a mixture of a catalytic element and a noble metal.

19. The system defined in claim 13 wherein said at least one second sensor element contains catalytic quantities of palladium, platinum, rhodium or gold.

20. The system defined in claim 1 wherein said second sensor includes at least one second sensor element formed by a heated molybdate semiconductor, a heated zirconium oxide semiconductor, or a Clark cell with a solid electrolyte provided at a gas inlet side with a finely divided transition metal catalyst and formed with at lest one electrode for measuring conductivity.

21. The system defined in claim 20 wherein said finely divided transition metal is platinum or palladium.

22. The system defined in claim 20 wherein said at least one second sensor element is a molybdate semiconductor containing bismuth or iron.

23. The system defined in claim 20 wherein said at least one second sensor element is a sintered molybdate body.

* * * * *

UNITED STATES PATENT AND TRADEMARK OFFICE
CERTIFICATE OF CORRECTION

PATENT NO. : 5,217,692
DATED : June 8, 1993
INVENTOR(S) : Hanns Rump & Claus-Dieter Kohl It is certified that error appears in the above-indentified patent and that said Letters Patent is hereby corrected as shown below:

On the title page, Item [30]: Foreign Application Data:
for " Aug. 8, 1990 [JP] Japan" read --Aug. 8, 1990 [DE] Fed. Rep. of Germany--
for " Aug. 31, 1990 [JP] Japan" read --Aug. 31, 1990 [DE] Fed. Rep. of Germany--;
for paragraph [22] of the heading, read: PCT filed Oct. 17, 1990--
insert additional paragraphs:--
[86] PCT No.: PCT/EP90/01752
§371 date: Jun. 10, 1991
§102(e) date: Jun. 10, 1991 --

Signed and Sealed this

Eighteenth Day of January, 1994

Attest:

BRUCE LEHMAN

*Attesting Officer*    *Commissioner of Patents and Trademarks*